United States Patent [19]

Grasser et al.

[11] Patent Number: 4,928,672
[45] Date of Patent: May 29, 1990

[54] SHOCKWAVE SOURCE HAVING A CENTRALLY DISPOSED ULTRASOUND LOCATING SYSTEM

[75] Inventors: Franz Grasser, Eggolsheim; Helmut Reichenberger, Eckental; Dietrich Hassler, Uttenreuth; Georg Naser, Zirndorf; Erhard Schmidt, Erlangen, all of Fed. Rep. of Germany

[73] Assignee: Siemens Aktiengesellschaft, Berlin and Munich, Fed. Rep. of Germany

[21] Appl. No.: 210,334

[22] Filed: Jun. 23, 1988

[30] Foreign Application Priority Data

Jul. 31, 1987 [DE] Fed. Rep. of Germany ....... 3725533
Aug. 19, 1987 [DE] Fed. Rep. of Germany ....... 3727691

[51] Int. Cl.$^5$ .............................................. A61H 1/00
[52] U.S. Cl. .................................... 128/24 A; 606/128
[58] Field of Search ................. 128/660.03, 24 A, 328; 367/142, 150, 174, 175; 606/127, 128

[56] References Cited

U.S. PATENT DOCUMENTS

| | | | |
|---|---|---|---|
| 4,539,989 | 9/1985 | Frossmann et al. | 128/328 |
| 4,617,931 | 10/1986 | Dory | 128/328 |
| 4,669,472 | 6/1987 | Eisenmenger | 128/328 |
| 4,674,505 | 6/1987 | Pauli et al. | 128/328 |
| 4,771,787 | 9/1988 | Wurster et al. | 128/660.03 |
| 4,803,995 | 2/1989 | Ishida et al. | 128/660.03 |

FOREIGN PATENT DOCUMENTS 3328039 3/1983 Fed. Rep. of Germany .

Primary Examiner—Kyle L. Howell
Assistant Examiner—K. M. Pfaffle
Attorney, Agent, or Firm—Hill, Van Santen, Steadman & Simpson

[57] ABSTRACT

A shockwave source of the type wherein a shockwave is generated by rapid electromagnetic repulsion of a membrane by a rapidly energized coil has a central opening extending through the membrane and the coil. An ultrasound head of an ultrasound transmission and reception system is received in the opening. The ultrasound head is disposed in a mount which is rotatable around its longitudinal axis by a rotary drive. In one embodiment of the shockwave source, the shockwave source also has a focusing device disposed in front of the membrane, and in this embodiment the focusing device also has a central opening in which the ultrasound head is received. The ultrasound head has a distal end in contact with a liquid coupling agent for promoting transmission to, and reception from, a patient to which the shockwave source is coupled. The shockwave source is particularly suited for lithotripsy treatment of gallstones.

12 Claims, 2 Drawing Sheets

SHOCKWAVE SOURCE HAVING A CENTRALLY DISPOSED ULTRASOUND LOCATING SYSTEM

BACKGROUND OF THE INVENTION

1. Field of the Invention

The present invention is directed to a shockwave source for extracorporeal treatment of a calculus disposed in the body of a patient by disintegrating the calculus with shockwaves, and in particular to such a shockwave source operating on the principle of a rapid electromagnetic repulsion of a membrane to generate the shockwaves.

2. Description of the Related Art

Shockwave generators are generally known in the art of the type having a coil mounted within a coil carrier and an electrically conductive membrane spaced from and insulated from the coil. Generally a sack filled with a fluid coupling agent is provided at a side of the shockwave source intended to be applied to a patient, with shockwaves generated by the membrane traveling through the coupling agent to the patient upon rapid energization of the coil, and the subsequent rapid repulsion of the membrane therefrom.

It is also generally known to make use of an ultrasound transmission and reception system combined with the shockwave generator to transmit an acoustic signal to the patient, and to receive echo signals from the patient, for locating and observing the calculus.

German OS 33 28 051 and corresponding to U.S. Pat. No. 4,674,505, discloses a shockwave generator having a shockwave tube in the form of a jacket, and a shockwave source of the type described above having a flat coil and a copper membrane separated therefrom by an insulating foil. An acoustic converging lens is disposed in the shockwave tube, and it focuses the planar shockwaves generated by the membrane to a focal point, and also forms the exit of the shockwave tube for the shockwaves. For applying the shockwave tube to the patient, the open portion of the tube lying opposite the membrane is closed with a sack which is filled with a coupling agent, as is the entire shockwave tube. The shockwave generator consisting of the shockwave tube and the shockwave source is moved toward a patient until the calculus to be disintegrated is situated in the focal point of the accoustic lens. The sack filled with coupling fluid is applied against the surface of the patient, so it is insured that the shockwaves always proceed within the fluid.

Published European application No. 0,081,639, corresponding to U.S. Pat. No. 4,539,989, discloses a locating device for a shockwave generator having two x-ray tubes with associated image intensifiers, or two ultrasound transducers, which are laterally attached to the shockwave generator. Using either the x-ray tubes or the ultrasound transducers, it is possible to observe the disintegration of the calculus during treatment. Locating of the calculus and adjustment of the shockwave generator relative thereto, however, are rendered more difficult due to the different irradiation directions of the shockwave generator and of the locating system. Moreover, because the locating system is laterally attached to the shockwave generator, the overall system is larger, so that manipulation thereof is more difficult.

Another shockwave generator is described in German OS No. 33 28 039, particularly in FIGS. 1 and 3 thereof. An ultrasound head of an ultrasound transmission and reception system for locating and observing the calculus is disposed next to or between a plurality of shockwave sources. This arrangement has the same disadvantages as the aforementioned arrangement in that the lateral placement of the ultrasound head requires additional structural volume, and under certain conditions this arrangement makes locating and observing the calculus more difficult.

Published European application 0 148 653, corresponding to U.S. Pat. No. 4,617,931, also discloses a shockwave source using an ultrasound locating system. In this structure, however, the shockwave source does not operate according to the electromagnetic repulsion principle. This shockwave source consists of a plurality, for example 300 or 400, of piezoelectric elements. Because each piezo-electric element can generate an acoustic pulse independently of the others, the omission of one or more of those elements does not significantly influence the operation of the shockwave source. For the purpose of ultrasound locating, it is therefore easily possible to replace one or more of the piezo-electric elements by the ultrasound probe or head of an ultrasound locating system.

A copending application relating in subject matter to the present application is U.S. Ser. No. 105,004, filed Oct. 6, 1987 (Reichenberger and Schittenhelm). This application is assigned to the same assignee as the present application. As shown in FIG. 3 of this related application, a shockwave generator is provided with a central opening in certain components of the shockwave source, with the transmission and reception head of an ultrasound locating device being received in the opening. In this structure, however, the ultrasound head does not project through the membrane, and the membrane remains at all times disposed between the ultrasound head and the patient. The ultrasound signals, both upon transmission and reception, must therefore pass through the membrane, and are attenuated thereby.

SUMMARY OF THE INVENTION

It is an object of the present invention to provide a shockwave generator for use in extracorporeal lithotripsy of a patient operating on the electromagnetic membrane repulsion principle which is constructed in a small and compact fashion and which enables precise observation of the calculus and localization of treatment of the calculus, and which is manipulatable in a simple manner.

The above objects are achieved in accordance with the principles of the present invention in an electromagnetic shockwave source wherein an ultrasound locating system having a standing plane is disposed in the shockwave source, with the axis of symmetry of the scanning plane being coincident with the central axis of the shockwave source, with no deterioration in the structural stability.

The shockwave source disclosed herein has a central opening in the coil carrier, the flat coil and in the conductive membrane, with the ultrasound head of an ultrasound transmission and reception system being received in these openings. The ultrasound waves and the shockwaves will thus always exhibit the same propogation direction, so that both systems are always simultaneously centered. Moreover, monitoring of the application of the sack to the patient can be undertaken with the assistance of the ultrasound waves, in addition to continuous observation of the calculus during disintegration thereof. Manipulation of the device is simplified because only one system is required to be adjusted as to position, this simultaneously positioning the other system. If the exit opening for the shockwaves in the shockwave generator disclosed herein is maintained the same size as the exit opening for a conventional shockwave generator without an ultrasound head, a larger acoustic irradiation area of the shockwaves into the patient is achieved using the shockwave generator disclosed herein, so that the sensation of pain experienced by the patient is reduced. The central arrangement of the ultrasound head in the shockwave generator also effects the linearization of the shockwaves, because the maximum which occurs in the middle of the shockwave generator is reduced.

The coil carrier, the flat coil and the conductive membrane may all be planar, and an acoustic focusing device may be provided for focusing the shockwaves to the calculus. The focusing device also has a central opening, in which the ultrasound head is received as well.

The ultrasound head is disposed in a mount aligned in the direction of the central axis of the shockwave source, and the mount may be rotatable around the central axis.

DESCRIPTION OF THE PREFERRED EMBODIMENTS

Figure 1:
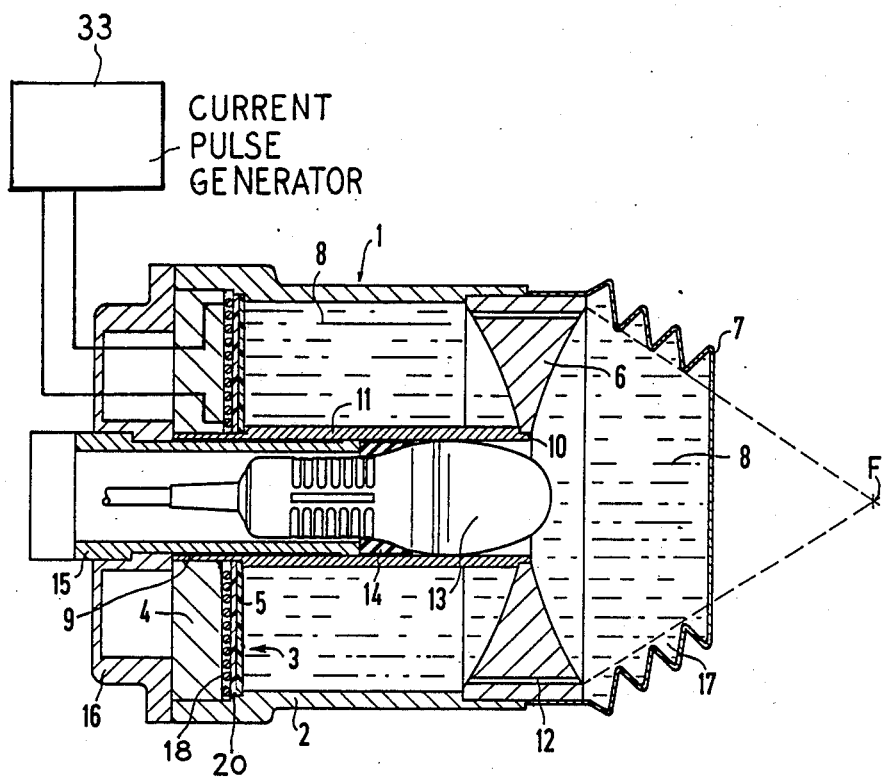
FIG. 1 is a side sectional view of a shockwave generator constructed in accordance with the principles of the present invention.

The embodiment of the shockwave generator 1 shown in FIG. 1 includes a shockwave tube 2 filled with a liquid, for example water. One open end of the shockwave tube 2 is terminated by a shockwave source 3, which includes a coil carrier 4 with a flat coil 18, therein connected to a current pulse generator 33, and a membrane 5 separated from the coil by insulating 20, which may be a part of or embedded in the coil carrier 4. The membrane 5 is maintained tightly pressed against the coil carrier 4 by a retaining ring or a ledge of the shockwave tube 2. The opposite open end of the shockwave tube 2 is covered by an acoustic lens 6, which is a converging lens. The shockwave tube 2, and the exit apperature for the shockwaves formed by the acoustic lens 6, are covered by a sack 7, forming a volume 17 which is filled with a coupling agent 8. The sack 7 is applied against the skin of a patient. As described below, the shockwave generator 1 is positioned relative to a calculus in the patient, such as a kidney stone or a gallstone, so that the focal point of the acoustic lens 6 is coincident with the calculus. The calculus can then be disintegrated by the shockwaves from the shockwave generator 1.

The shockwave source 3 and the acoustic lens 6 of the shockwave generator 1 have respective central openings 9 and 10, the openings 9 and 10 being connected by a tube 11. The remainder of the volume between the shockwave tube 2, the tube 11, the shockwave source 3 and the acoustic lens 6 is filled with the same coupling agent 8 which is present in the sack 7 by means of channels 12 in the acoustic lens 6.

An ultrasound head is introduced into the tube 11 from a rear of the shockwave source 3, and the head 13 partially projects into the volume 17 defined by the acoustic lens 6 and the sack 7. The ultrasound head 13 is provided with a seal 14 relative to the tube 11, so that no coupling agent 8 can escape. The seal 14 and the rear portion of the ultrasound head 13 are held by a tubular mount 15, which is connected to a cover cap 16 for the rear of the shockwave source 3.

The shockwave source 3 of the shockwave generator 1 produces planar shockwaves in a known manner which are focused to the focal point by the acoustic lens 6. The ultrasound head 13, which may be, for example, a sector scanner, is centrally arranged in the shockwave generator 1, so that the central or longitudinal axis of the ultrasound head 13 is also aligned to the focal point. The focal point is thus always covered by the ultrasound waves from the ultrasound head 13, regardless of the rotational orientation of the ultrasound head 13, and thus regardless of the direction of the ultrasound fan (sector) shaped beam. The ultrasound head 13 can thus be rotated to cover the calculus with the ultrasound beam, so that the calculus is visible on a monitor (not shown). The shockwave generator 1 can be displaced in the scan direction until the calculus is situated in the focal point of the shockwave generator 1, lying on the central axis of the ultrasound head 13.

During adjustment of the shockwave generator 1, the application of the sack 7 to the patient can be simultaneously monitored, so that an optimum application procedure is always guaranteed. The success of the calculus disintegration can also be observed using the ultrasound head 13 during shockwave treatment. The shockwave generator disclosed herein is particularly suited for treatment of gallstones situated in the gall bladder, these gallstones being transparent to x-rays.

Figure 2:
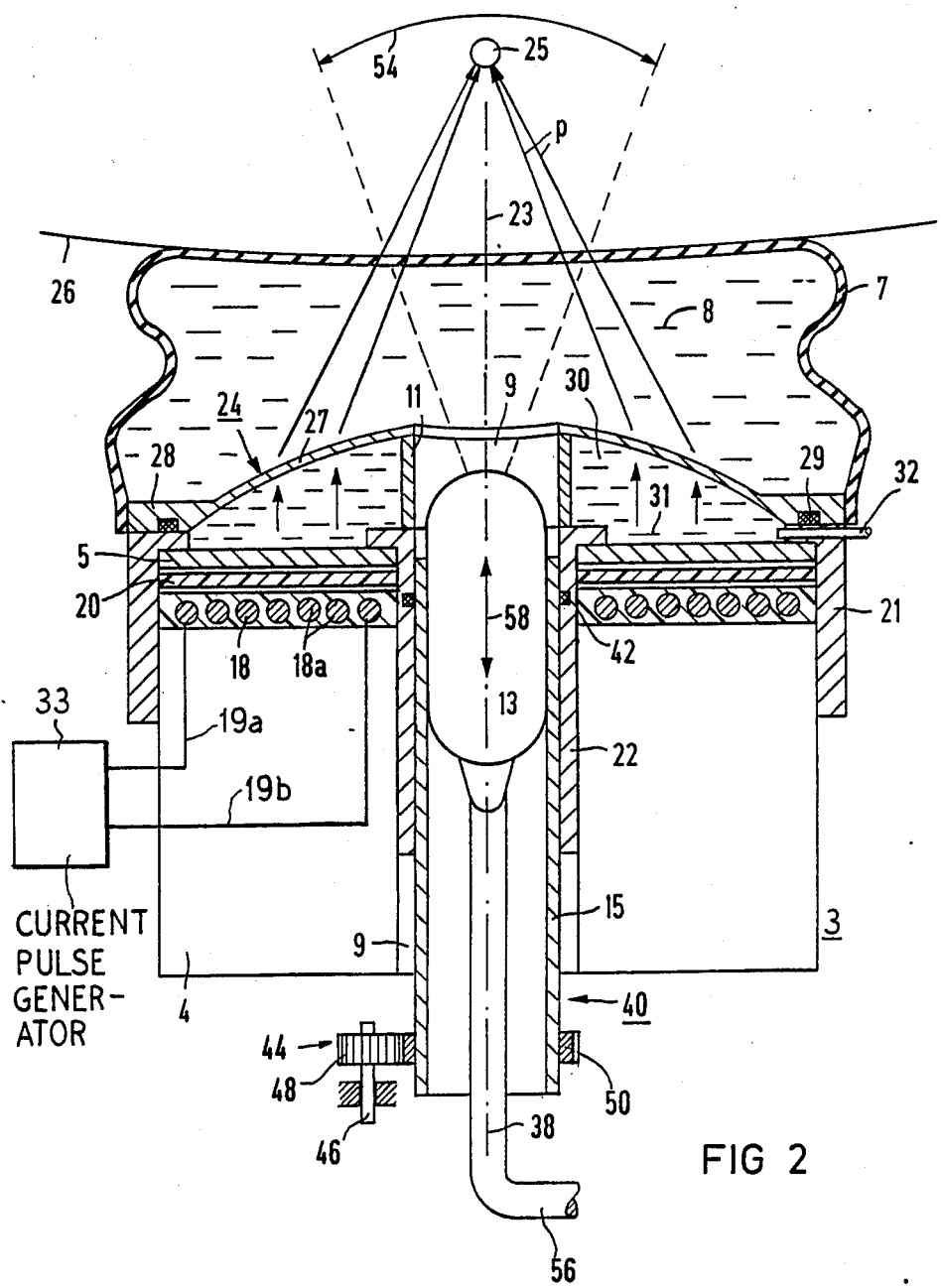
FIG. 2 is a side sectional view of a further embodiment of a shockwave generator constructed in accordance with the principles of the present invention.

In the embodiment of the shockwave generator shown in FIG. 2, the coil carrier 4 is in the form of a cylinder. The carrier 4 has a central cylindrical opening 9 which is symmetrical relative to a central axis 23 of the shockwave source 3. The coil carrier 4 preferrably consists of ceramic material. A planar flat coil 18 is disposed at one planar side of the coil carrier 4. The coil 18 has spiral windings 18a held in a plastic casting occupying the entire planar side of the coil carrier 4. The coil 18 has two electrical leads 19a and 19b connected to a current pulse generator 33, and also has a central opening in registry with the central opening 9 of the coil carrier 4.

An insulating foil 20 is attached to the flat coil 18 at a side thereof opposite the coil carrier 4. The insulating foil 20 also has a central opening in registry with the central opening 9. The foil 20 is preferrably glued to the flat coil 18. An annular electrically conductive membrane 5, which may consist of metal, is disposed directly adjacent the insulating foil 20, and also has a central opening in registry with the central opening 9. Close contact between the insulating foil 20 and the membrane 5 is assured in a known manner by maintaining a pressure acting on the side of the membrane 5 facing the insulating foil 20 which is less than the pressure acting on the other side of the membrane 5.

The coil carrier 4, the flat coil 18, the insulating foil 20 and the membrane 5 are rigidly connected at their respective outer edges to a first annular retainer 21. In a similar manner, the carrier 4, the coil 18, the foil 20 and the membrane 5 are rigidly connected at their respective central openings with a second annular retainer 22. The retainers 21 and 22 assure that the membrane 5 is maintained immobile at its edges relative to the flat coil 18.

The coil carrier 4, the flat coil 18, the insulating foil 20, the membrane 5 and the retainers 21 and 22 form the core of the electromagnetic shockwave source 3. As noted above, the central axis 23 of the shockwave source 3 is coincident with the central axis of the opening 9 in the coil carrier 4, and the respective centers of the other openings in the other components in registry therewith. When a rapidly changing current, such as a steep current pulse from a capacitor discharge, is supplied from the current pulse generator 33 via the leads 19a and 19b, so that the current flows through the coil 18, a current is thereby induced in the electrically conductive membrane 5. The current in the coil 18 and the current in the membrane 5 each generate a magnetic field, causing the membrane 5 to be rapidly repelled from the flat coil 18. The membrane 5 exhibits an excursion between the retainers 21 and 22 in a direction toward the patient, and thus generates an acoustic pulse which is subsequently shaped into a shockwave p.

A focusing device 24 is connected to the electromagnetic shockwave source 3. In this embodiment, the focusing device 24 is a plano-convex acoustic liquid lens, which focuses the essentially planar acoustic pulses to a calculus 25 in the patient 26, for example a kidney stone or a gallstone. The focusing device 24 also has a central opening in registry with the central opening 9. The planar, rear face of the focusing device 24 is formed by the membrane 5. The convex face of the focusing device 24 is formed by a calotte-shaped cap 27. The cap 27 consist of a structurally rigid plastic, such as polystyrol. The cap 27 may alternatively consist of polymethylmethacrylate (PMMA) or polyethylene. The cap 27 also has a central opening in registry with the central opening 9, and the other central openings in the components.

At its outer edge, the cap 27 has (or merges into) a flange 28. The cap 27 is held in place by screws (not shown) or other fasteners acting on the flange 28. It is also possible to glue the flange 28 to the retainer 21. The flange 28 preferably has an O-ring 29 as a seal.

A tube 11 is disposed between the central opening of the cap 27 and the second retainer 22. The tube 11, for example, may have one end glued to the cap 27, and an opposite end glued to the retainer 22. An interior volume 30 is thus formed limited by the membrane 5, the cap 27, the tube 11 and the retainers 21 and 22. This interior volume 30 can be filled with a liquid 31 via a line 32. A further opening (not shown) may also be provided which permits a circulation of the liquid 31.

Sealing of the interior volume 30 is insured by O-ring 29 situated in a groove in the connecting flange 28.

The sack 7 which is filled with the coupling agent 8, for example a liquid such as degasified water, is secured to the edge of the connecting flange 28. This permits good acoustic application of the shockwave source 3 to the patient 26.

The liquid 31 in the interior volume 30 of the focusing device 24 is selected so that the speed of sound therein is not significantly lower than the speed of sound in water. The liquid 31 is preferably a halogenated hydrocarbon compound such as, for example, carbon tetrachloride, or a completely fluoridated hydrocarbon. The liquid 31 may also be a silicone.

The tubular mount 15 is disposed inside the retainer 22. The tubular mount 15 is rotatable around its longitudinal axis 38. The longitudinal axis 38 is coincident with the central axis 23 of the shockwave source 3. The tubular mount 15 is part of a water-tight rotary transmission system 40. The system 40, in addition to the tubular mount 15, includes a seal 42 and a rotary drive generally referenced at 44. The seal may be an O-ring sitauted in a groove of the retainer 22. The seal 42 prevents the coupling agent 8 from leaking from the sack 7 via the rotary transmission system 40. The rotary drive 44 includes a driveshaft 46 having a gear 48 at an end thereof engaging a ring gear 50 attached to the tubular mount 15. The ring gear 50 may extend around the full circumference of the tubular mount 15, or only a portion thereof.

The rotary transmission system 40 is secured in any suitable manner against axial dislocation, the details of which are not shown in FIG. 2.

The ultrasound head 13 of a conventional ultrasound transmission and reception system is disposed in the tubular mount 15 in a liquid-tight fashion. The ultrasound head 13 is preferably an applicator for a sector scan. The angle of the sector scan is indicated by the curved double arrow 54. The longitudinal axis of the ultrasound head 13 and the central axis 23 of the shockwave source 3 are coincident.

The ultrasound head 13 is connected to the ultrasound transmission and reception system via an electrical line 56. At its distal end, the ultrasound head 13 is in contact with the coupling agent 8. The ultrasound head 13 is displacable inside the tubular mount 15 in the direction of the central axis of the shockwave source, as indicated by the straight double arrow 58. For this purpose, the ultrasound head 13 may be attached, for example, in a further mount (not shown in FIG. 2) which is in turn displaceably arranged in the tubular mount 15.

The respective units shown in FIGS. 1 and 2 may be secured to a retaining arm or stand in a known manner, which is not shown in greater detail in the drawings The retaining arm enables a precise positioning and fixing of the shockwave source 3 relative to the patient 26.

The presence of the opening 9 will result in a loss of acoustic power of the shockwave source 3, however, this loss is minimal, and therefore acceptable, for two reasons. First, the central region of the electromagnetic shockwave source 3 contributes relatively little to the overall power output. Second, the central portion of a conventional plano-convex focusing device has the greatest attenuating effect, and this central portion is absent in the focusing device 24. A precise, high-resolution observation of the region of the patient in front of the shockwave source 3, and a precise alignment of the shockwave source 3 relate to the calculus 25, are possible using a sector scan applicator as the ultrasound head 13.

Other advantages of the apparatus are a compact structure and an exact ultrasound observation of the calculus 25 during treatment with the shockwaves p which are obtainable directly from the direction of propogation of the shockwaves p.

Although modifications and changes may be suggested by those skilled in the art it is the intention of the inventors to embody within the patent warranted hereon all changes and modifications as reasonably and properly come within the scope of their contribution to the art.

We claim:

1. A shockwave generator for extracorporeal disintegration of a calculus in a patient comprising:
   a housing:
   a flat coil in said housing having a central opening therein;
   an electrically conductive membrane having a central opening therein;
   means for insulating said membrane from said coil and having a central opening therein;
   means for applying a current pulse to said coil to cause said membrane to be rapidly repelled therefrom, thereby generating a pressure pulse;
   means in said housing adapted for focussing said pressure pulse to a calculus in a patient;
   means in said housing disposed between said membrane and said patient adapted for coupling said pressure pulse into said patient;
   ultrasound means for transmitting and receiving ultrasound signals to and from said patient, all of said central openings of said coil, said membrane and said means for insulating being in registry, and said ultrasound means having an ultrasound head received in said central openings.

2. A shockwave generator as claimed in claim 1 wherein said means for focusing has a central opening in registry with said central openings in said coil, said membrane and said means for insulating, and wherein said ultrasound head of said ultrasound means is also received in said central opening of said means for focusing.

3. A shockwave generator as claimed in claim 1 wherein said means for focusing is an acoustic lens.

4. A shockwave generator as claimed in claim 1 wherein said ultrasound means is an ultrasound sector scanner, and wherein said ultrasound head is a sector scan applicator.

5. A shockwave generator claimed in claim 1 wherein said shockwave generator has a central axis extending through said central opening, and further comprising means for displacing said ultrasound head in the direction of said central axis.

6. A shockwave generator as claimed in claim 1, wherein said means for coupling is a flexible sack, adapted for contact with said patient, filled with material for propagating said pressure pulse, and wherein said ultrasound head is disposed in said openings in contact with said material.

7. A shockwave generator as claimed in claim 1 wherein said shockwave source has a central axis and wherein said ultrasound head has a longitudinal axis, and further comprising means for mounting said ultrasound head in said central openings with said longitudinal axis and said central axis coinciding.

8. A shockwave generator as claimed in claim 7, wherein said means for mounting is a means for liquid-tight mounting of said ultrasound head.

9. A shockwave generator as claimed in claim 7 further comprising retainer means for holding said coil, said membrane and said means for insulating adjacent each other disposed in said central opening, said means for retaining having a central opening therein and said means for mounting being disposed in said central opening of said means for retaining.

10. A shockwave generator as claimed in claim 7 further comprising means for rotating said means for mounting around said central axis.

11. A shockwave generator as claimed in claim 10 wherein said means for mounting comprises:
    a cylindrical tube extending through said openings; and
    rotary drive means engaging said cylindrical tube for rotating said tube around said central axis.

12. A shockwave generator for extracorporeal disintegration of a calculus in a patient comprising:
    a housing;
    a flat coil in said housing having a central opening therein;
    an electrically conductive membrane having a central opening therein;
    means for insulating said membrane from said coil and having a central opening therein;
    means for applying a current pulse to said coil to cause said membrane to be rapidly repelled therefrom, thereby generating a pressure pulse propagating along a central axis, said respective central openings of said flat coil, said electrically conductive membrane and said means for insulating being in registry;
    means in said housing adapted for focussing said pressure pulse to a calculus in a patient;
    means in said housing disposed between said membrane and said patient adapted for coupling said pressure pulse into said patient;
    ultrasound means for transmitting and receiving ultrasound signals to and from said patient, said ultrasound means including an ultrasound head having a longitudinal axis;
    retainer means for holding said coil, said membrane and said means for insulating adjacent each other disposed in said central opening, said means for retaining having a central opening therein;
    means for mounting said ultrasound head in said central opening of said retaining means with said longitudinal axis and said central axis coinciding;
    means for rotating said means for mounting around said central axis; and
    means for displacing said ultrasound head along said central axis.

* * * * *